United States Patent
Ford

(10) Patent No.: US 6,461,600 B1
(45) Date of Patent: Oct. 8, 2002

(54) TOPICAL PAIN RELIEF COMPOSITION AND CARRIER

(76) Inventor: Peter R. Ford, 544 St. George Blvd., Moncton, NB (CA), E1E 2B5

( * ) Notice: Subject to any disclaimer, the term of this patent is extended or adjusted under 35 U.S.C. 154(b) by 0 days.

(21) Appl. No.: 09/904,082

(22) Filed: Jul. 12, 2001

(30) Foreign Application Priority Data

Jul. 19, 2000 (CA) .............................................. 2315815

(51) Int. Cl.$^7$ ................................................ A61K 31/74

(52) U.S. Cl. ................................ 424/78.02; 424/78.06; 514/817

(58) Field of Search ........................... 424/78.02, 78.06; 514/817

(56) References Cited

U.S. PATENT DOCUMENTS

| 4,148,914 | | 4/1979 | Szmuszkovicz |
| 5,972,359 | * | 10/1999 | Sine et al. .................. 424/401 |

* cited by examiner

*Primary Examiner*—Carlos Azpuru
(74) *Attorney, Agent, or Firm*—Spencer Fane Britt & Browne LLP

(57) ABSTRACT

A cream carrier is provided which has use as a cream-type carrier for topical delivery of medicaments including analgesics. The carrier comprises a mixture of: squalane NF, an emulsifier such as Tween 80, glycerin, cetyl alcohol NF, glyceryl monostearate, lecithin organogel preserved, BHT, urea USP, EDTA, water, stearic acid, simethicone USP, and ethoxy diglycol reagent. The invention also comprises a combination of the carrier, with either or both of ketamine hydrochloride and amitriptyline hydrochloride, which has use as a topically applied analgesic.

14 Claims, No Drawings

TOPICAL PAIN RELIEF COMPOSITION AND CARRIER

Priority benefit under 35 U.S.C. §119 is claimed to Canadian patent application Ser. No. 2,315,815 filed Jul. 19, 2000.

FIELD OF THE INVENTION

The invention relates to topical pain relief compositions for applying to the skin of a patient, and to cream-type carrier compositions or bases for use with topical pain relief medicaments.

BACKGROUND OF THE INVENTION

It has been proposed to use compounds for topical pain relief which have not had widespread use as such, such as ketamine and amitriptyline. These compounds may provide pain relief in some circumstances when applied topically. However, it has been found that their use as topical pain relief medicaments is highly dependent on the selection of a suitable carrier. Previous proposals have related to mixing such medicaments with a cream-type base, for applying on the skin of a patient. However, suitable topical pain relief properties of these compounds require admixture with a carrier which achieves a suitable delivery to the skin of a patient. Improved delivery of such medicaments may be achieved with a suitable carrier having enhanced properties for delivering the medicinal compounds to the skin of a patient in a manner which enhances absorption by the patient's skin over a suitable period of time.

The invention further relates to an improved method for preparing a cream-based carrier for use with a topical pain relief medication such as ketamine or amitriptyline.

The present invention relates to an improved composition for topically delivering medicaments, including medicaments having analgesic properties, such as ketamine, which results in a more profound pharmacological effect than cream-type carriers previously proposed.

The use of amitriptyline hydrochloride, e.g., N-(2-amino cycloaliphatic) benzamides and napthamides, for pain relief is known. See e.g. U.S. Pat. No. 4,148,914 by Szmuszkovicz. Likewise, ketamine hydrochloride is known to have a variety of medical uses. Use of such compounds for topical application for pain relief has been limited by an inability to provide a suitable and effective carrier.

DESCRIPTION OF THE INVENTION

In one aspect, the invention comprises a pharmaceutical carrier for topical application of medicaments, consisting of a cream-type base comprising a mixture of the following:

squalane NF
emulsifier (e.g. Tween 80)
glycerin
cetyl alcohol NF
glyceryl monostearate
lecithin organogel preserved
BHT (preferably a 10% aqueous solution)
urea USP
EDTA (preferably a 5% aqueous solution)
water
stearic acid (preferably stearic acid NF flakes)
antifoaming agent (preferably simethicone Med. Antifoam "A" compound)
Ethoxy diglycol reagent In another aspect, the invention comprises a mixture of the carrier described above, with ketamine hydrochloride in the amount of between 3 mg per ml and 150 mg per ml. Particularly preferred is ketamine hydrochloride in the amount of 5 mg per ml.

In another aspect, the mixture comprises the above carrier, with two active ingredients, namely ketamine hydrochloride in the amount of between 3 mg per ml and 150 mg per ml, with a preferred strength of 5 mg per ml, and amitriptyline chloride in the amount of between 5 mg/ml and 20 mg/ml, with a preferred amount of 10 mg per ml of carrier.

In a third aspect, the invention comprises the above carrier, with amitriptyline in the amount of between 5 mg/ml and 20 mg/ml, with a particularly preferred amount of 10 mg per ml of carrier.

All quantities expressed herein may be varied within a range of ten percent.

The invention will now be described by reference to examples illustrative of preferred compositions and methods for preparing same.

EXAMPLE 1

Carrier Mixture

In a preferred aspect, the cream-type carrier mixture consists of the following quantities of the following ingredients:

| | |
|---|---|
| Squalane NF | 40 gm |
| Tween 80 | 60 ml |
| Glycerin USP synthetic | 80 ml |
| Cetyl alcohol NF | 80 gm |
| Glyceryl monostearate (pure) | 120 gm |
| Lecithin organogel preserved | 80 ml |
| BHT 10% solution | 20 ml |
| Urea USP | 100 gm |
| EDTA 5% solution | 40 ml |
| Water, purified | 1150 ml |
| Stearic acid NF Flakes (Triple pressed) | 80 gm |
| Simethicone USP (Med. Antifoam "A" compound) | 20 ml |
| Ethoxy diglycol reagent | 200 ml |

The above mixture may be scaled up or down in quantity while maintaining the same ratio of the ingredients to each other, in order to prepare larger or smaller batches of the cream-type carrier base.

EXAMPLE 2

Preparation of lecithin organogel (preserved).

Lecithin organogel (preserved) is prepared by the following protocol: 500 gm of soya lecithin (granular) and 500 ml of isopropyl myristate NF are measured. The two are combined in a beaker, and permitted to stand overnight at room temperature until totally dissolved in solution. The mixture is then heated gradually to 40° C., while stirring. 2 gm sorbic acid NF powder is then added and stirred until dissolved.

EXAMPLE 3

Preparation of carrier mixture.

Step 1:

The compounds listed in example 1 are prepared and measured out. The urea USP is dissolved in the water and the EDTA solution is added thereto. Optionally, the mixture may be warmed, and then permitted to cool to room temperature (21° C.).

Step 2:

Tween 80 and glycerin are combined at 21° C.

Step 3:

The following are combined: Cetyl alcohol, glyceryl monostearate, stearic acid, lecithin organogel, BHT solution, squalane and ethoxy diglycol; this mixture is heated to solution in a tared beaker while stirring with a spin bar to a maximum temperature of 50° C.

Step 4:

While the mixture of step 3 is being stirred with the spin bar, the mixture of step 2 is slowly added. The water solution in step 1 is then added, at room temperature, and then the simethicone. The resulting mixture is stirred with a spin bar until congealed.

Step 5:

The resulting mixture is allowed to sit overnight twelve hours at room temperature.

The resulting cream is a creamy white beige, that also exhibits pearlescent character. It has a nutty smell. It is stable for periods of up to 12 months. It is a thick appearing cream-gel consistency, that is completely uniform in appearance. It also exhibits good spreadability when applied to intact skin.

The resulting cream may be stored at room temperature until needed, at which time it is then combined with an active ingredient such as ketamine.

EXAMPLE 4

Preparation of ketamine/carrier mixture.

0.3750 gm ketamine hydrochloride USP, is wetted with 1.5 ml of ethoxy diglycol reagent, and stirred into 75 gm of the base cream prepared as per example 3 and triple milled. A cream-type preparation results which contains ketamine hydrochloride @ 5 mg/ml.

EXAMPLE 5

Preparation of amitriptyline/ketamine/carrier mixture.

0.3750 gm ketamine hydrochloride USP and 0.750 gm amitriptyline hydrochloride USP are combined and wetted with 2.0 ml of ethoxy diglycol reagent, and stirred into 75 gm of the base cream prepared as per example 3 and triple milled. The cream-type mixture contains ketamine hydrochloride at 5 mg/ml and amitriptyline hydrochloride at 10 mg/ml.

EXAMPLE 6

Preparation of amitriptyline/carrier mixture.

0.750 gm amitriptyline hydrochloride USP, is wetted with 1.5 ml of ethoxy diglycol reagent, and stirred into 75 gm of the base cream prepared as per example 3 and triple milled. A cream-type preparation results which contains amitriptyline hydrochloride @ 10 mg/ml Mixtures of carrier and active ingredient as described in the above examples, may be applied topically by various applicators, including:

a. Topical syringes manufactured by Baxa Corp.
b. PVC applicator jars that are single walled, manufactured by EMP Germany.
c. PVC tubes, that are subsequently heat sealed after filling.

Preparations according to the present invention are suitable for treatment of the following conditions:

Pain and pain-related conditions, including: intractable pain that is non-responsive to opioids; myofascial pain, postherpetic neuralgia, neuropathic pain, complex regional pain syndrome type I(CRPS I) (formerly called reflex sympathetic dystrophy), pain secondary to metastatic lesions, fibromyalgia, diabetic peripheral neuropathy, post-surgical neuropathy, post-trauma neuropathy, visceral neuropathy, xenobiotic neuropathies, and idiopathic neuropathies.

What is claimed is:

1. A cream carrier for a topically-applied medicament, comprising a mixture of:

squalane NF
emulsifier
glycerin
cetyl alcohol NF
glyceryl monostearate
lecithin organogel preserved
BHT
urea USP
EDTA
water
stearic acid
antifoaming agent
ethoxy diglycol reagent.

2. A cream carrier as defined in claim 1, comprising the following components, prepared in any quantity by maintaining equivalent ratios:

| | |
|---|---|
| squalane NF | 40 gm |
| Tween 80 | 60 ml |
| glycerin | 80 ml |
| cetyl alcohol NF | 80 gm |
| glyceryl monostearate | 120 gm |
| lecithin organogel preserved | 80 ml |
| BHT | 2 ml |
| urea USP | 100 gm |
| EDTA | 2 ml |
| water | 2010 ml |
| stearic acid NF Flakes | 80 gm |
| simethicone USP | 20 ml |
| ethoxy diglycol reagent | 200 ml | wherein the amounts of any of said components may vary by plus or minus up to 10%.

3. A cream carrier according to claim 1, comprising a carrier for an analgesic medicament.

4. A cream carrier according to claim 1, further comprising a medicament selected from one or both ketamine hydrochloride and amitriptyline hydrochloride.

5. A cream carrier according to claim 4, comprising ketamine hydrochloride in the amount of between 3 and 150 mg per ml of carrier.

6. A cream carrier according to claim 5, comprising ketamine hydrochloride in the amount of between 4.5 and 5.5 mg per ml of carrier.

7. A cream carrier according to claim 4, further comprising amitriptyline hydrochloride at between 5 mg and 20 mg per ml of carrier.

8. A cream carrier according to claim 7, wherein said amitriptyline hydrochloride is in the amount of between 9.0 and 11.0 mg per ml of carrier.

9. A cream carrier according to claim 2 wherein at least one of said BHT and EDTA comprises an aqueous solution.

10. A method of preparing a cream-based carrier for a topically-applied medicament, comprising the steps of:

a) dissolving 100 gm of urea in water;

b) adding 2 ml EDTA;

c) combining an effective amount of an emulsifier and 80 ml of glycerin at 21° C.;

d) combining 80 gm cetyl alcohol, 120 gm glyceryl monostearate, 80 gm stearic acid, 80 ml lecithin organogel preserved, 2 ml BHT, 40 gm squalane and 200 ml ethoxy diglycol reagent, and heating to solution while spinning, to a maximum temperature of 50° C.;

e) combining the emulsifier and cetyl alcohol mixtures, while mixing together, and adding urea mixture while stirring;

f) adding water, such that the total volume of water added in steps (a) and (f) is 1150 ml;

g) adding simethicone 20 ml, and mixing until congealed;

h) permitting said mixture to sit at room temperature for at least 8 hours;

wherein any of said amounts expressed above may be varied by up to 10%, and wherein any amount of said carrier may be prepared by maintaining equivalent ratios of said components to scale up or down said method.

11. A method according to claim 10 wherein said emulsifier comprises 60 ml of Tween 80.

12. A method according to claim 10, wherein said carrier is for an analgesic medicament.

13. A method according to claim 9, wherein at least one of said EDTA and BHT is in an aqueous solution when added to said carrier.

14. A method according to claim 12, wherein said analgesic medicament is selected from ketamine hydrochloride, amitriptyline hydrochloride, and a combination of ketamine hydrochloride and amitriptyline hydrochloride.

* * * * *